United States Patent [19]
Roos et al.

[11] Patent Number: 6,136,819
[45] Date of Patent: Oct. 24, 2000

[54] ANNELATED DIHYDROPYRIDINES AND THE USE THEREOF FOR PREPARING PHARMACEUTICAL PREPARATIONS

[75] Inventors: Otto Roos, Schwabenheim; Walter Lösel, Gau-Algesheim; Dietrich Arndts, Appenheim, all of Germany

[73] Assignee: Boehringer Ingelheim GmbH, Ingelheim, Germany

[21] Appl. No.: 09/329,443

[22] Filed: Jun. 10, 1999

Related U.S. Application Data

[62] Division of application No. 08/857,643, May 16, 1997, Pat. No. 5,968,948, which is a division of application No. 08/360,867, Dec. 21, 1994, Pat. No. 5,661,157.

Foreign Application Priority Data

Dec. 21, 1993 [DE] Germany ................... 4343683

[51] Int. Cl.⁷ .................... C07D 471/04; A61K 31/44
[52] U.S. Cl. .................. 514/292; 546/84; 546/114; 514/301
[58] Field of Search .................. 544/163; 546/139.14, 546/148.147, 149.9, 84, 114; 514/255.307, 292, 301

[56] References Cited

U.S. PATENT DOCUMENTS

| | | | |
|---|---|---|---|
| 5,500,431 | 3/1996 | Audia et al. | 514/280 |
| 5,665,729 | 9/1997 | Losel et al. | 514/292 |
| 5,686,462 | 11/1997 | Losel et al. | 514/292 |

FOREIGN PATENT DOCUMENTS

| | | | |
|---|---|---|---|
| 0 037 934 | 10/1981 | European Pat. Off. . | |
| 0 251 194 | 1/1988 | European Pat. Off. . | |
| 0 288 048 | 10/1988 | European Pat. Off. . | |
| 358957 | 8/1989 | European Pat. Off. | 546/139 |
| 0 358 957 | 3/1990 | European Pat. Off. . | |
| 30 23 717 | 1/1981 | Germany . | |
| 92/11010 A1 | 7/1992 | WIPO . | |

OTHER PUBLICATIONS

Arai et al., Chemical Abstracts, vol. 68, No. 19, Abstract 94351u (May 6, 1998).
Chemical Abstracts, vol. 95, No. 11, Abstract 97842y (Sep. 14, 1981).
Hirai et al., Heterocycles, vol. 25, pp. 201–204 (1987).
Kansal et al., Indian Journal of Chemistry, vol. 20B, Oct. 1981, pp. 885–890.

*Primary Examiner*—Zinna Northington Davis
*Attorney, Agent, or Firm*—Robert P. Raymond; Alan R. Stempel; Mary-Ellen M. Devlin

[57] ABSTRACT

Compound of general formula I

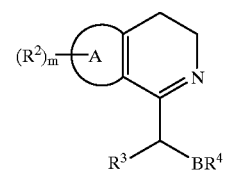

wherein

A denotes a benzo, indolo or thienyl group;

B denotes the group —O—, —S— or —CHR⁵—, wherein $R^5$ is hydrogen, $(C_{1-6})$alkyl, phenyl or benzyl;

$R^3$ denotes 2- or 3-thienyl, $(C_{4-7})$cycloalkyl, $(C_{4-6})$ cycloalkyl$(C_{1-5})$alkyl or

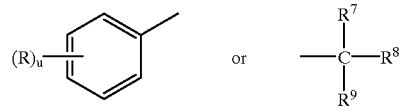

wherein R is $(C_{1-4})$alkyl, hydroxy, —N₃, halogen (F, Cl, Br, I), $CF_3$ or $(C_{1-4})$alkoxy, u is 0, 1, 2 or 3, and m, $R^2$, $R^4$, $R^7$, $R^8$ and $R^9$ are as defined in the specification, as well as pharmaceutical preparations containing these compounds and the pharmaceutical use thereof.

5 Claims, No Drawings

ANNELATED DIHYDROPYRIDINES AND THE USE THEREOF FOR PREPARING PHARMACEUTICAL PREPARATIONS

RELATED APPLICATIONS

This is a division of U.S. application Ser. No. 08/857,643, filed May 16, 1997, now U.S. Pat. No. 5,968,948, which is a division of U.S. application Ser. No. 08/360,867, filed Dec. 21, 1994, now U.S. Pat. No. 5,661,157.

The invention relates to new annelated dihydropyridinoacetic acid derivatives, processes for preparing them and pharmaceutical compositions containing these compounds.

Dihydroisoquinolines are known from EP-A 37 934. The compounds specified therein are cardiotonically active and have the effects of increasing contractility and influencing blood pressure. They have been proposed for improving blood circulation through the tissues and for improving the oxygen supply to the tissues. These possible uses are based on the vascular activity of the compounds. EP-A 251 194 and EP-A 288 048 describe how carbocyclically and heterocyclically annelated dihydropyridines have a cardioprotective or cerebroprotective activity and constitute an entirely new type of Ca-antagonistic compounds. WO 91/11010 describes the use of such compounds for cerebroprotective agents, for treating chronic inflammatory processes and for inhibiting blood clotting and blood platelet aggregation.

The present invention relates to new carbocyclically and heterocyclically annelated dihydropyridines and the pharmaceutical use of these compounds. The new compounds have valuable therapeutically useful properties. They may be used as cardioprotective agents, as cerebroprotective agents (particularly for treating patients who have suffered a stroke or are in danger of suffering a stroke) and as agents for treating chronically inflammatory processes (e.g. bronchial asthma and arthritis). These compounds may also be used as agents with an antiproliferative effect and as agents for treating ulcerative colitis and Crohn's disease.

The invention relates to compounds of general formula I

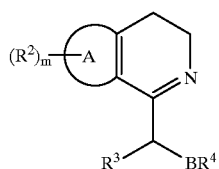

wherein

A denotes a benzo, indolo or thieno group; wherein, if A is benzo, m is 2 or 3 (preferably 2, whilst the two $R^2$s are in positions 6 and 7) and the substituents $R^2$ independently of each other denote hydroxy, $(C_{1-4})$ alkoxy, benzyloxy, halogen (F, Cl, Br, I), $(C_{1-4})$alkyl, methanesulphonyloxy or methanesulphonamido, or two adjacent substituents $R^2$ may together represent —O—$CH_2$—O— or —O—$CH_2$—$CH_2$—O—; and if A is indolo or thieno, m is zero;

B represents the group —O—, —S— or —$CHR^5$—, wherein $R^5$ is hydrogen, $(C_{1-6})$alkyl, phenyl or benzyl;

$R^3$ denotes 2- or 3-thienyl, $(C_{4-7})$cycloalkyl, $(C_{4-6})$-cycloalkyl$(C_{1-5})$alkyl or

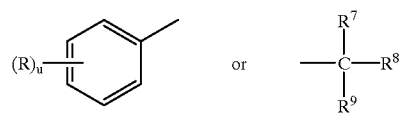

wherein
R is $(C_{1-4})$alkyl, hydroxy, —$N_3$, halogen (F, Cl, Br, I), $CF_3$ or $(C_{1-4})$alkoxy,
u is 0, 1, 2 or 3, and
$R^7$, $R^8$ and $R^9$ independently of one another may represent methyl, ethyl, propyl, phenyl or benzyl, but not more than two of the substituents can simultaneously represent phenyl or benzyl);

$R^4$ denotes
(a) branched or unbranched $C_{3-6}$-alkenyl which may be substituted by phenyl, or
(b) branched or unbranched $C_{3-6}$-alkynyl which may be substituted by phenyl, or
(c) branched or unbranched $C_{1-13}$-alkyl, wherein the alkyl may be substituted by
hydroxy, $(C_{1-4})$alkoxy,
di$(C_{4-4})$alkylamino,
furyl,
pyridyl,
pyrrolidinyl, N-methylpyrrolidinyl,
morpholino,
indolyl,
nitrilo,
thienyl,
adamantyl,
cyclohexyl,
phenoxy,
benzyloxy,
naphthyloxy or
phenyl,
(whilst this phenyl or the phenyl contained in the phenoxy group or benzyloxy group may be mono-, di- or trisubstituted by hydroxy, $(C_{1-4})$ alkoxy, benzyloxy, halogen (F, Cl, Br, I), $CF_3$, $N_3$, $NO_2$, $(C_{1-4})$alkyl, adamantyl, —$SO_2NH_2$, $NHCOCH_3$, —$NHSO_2CH_3$ or —C(O)O—$R_{14}$, [wherein $R_{14}$ is $(C_{3-7})$cycloalkyl or branched or unbranched $(C_{1-6})$alkyl, whilst the alkyl may be substituted by phenyl, and this phenyl may be mono- to trisubstituted by halogen (F, Cl, Br, I), $CF_3$, $C_1$- or $C_2$-alkyl, $C_1$- or $C_2$-alkoxy]
or may be substituted by the bridge —O—$CH_2$—O—), or
by 2 unsubstituted phenyl groups;
(d)

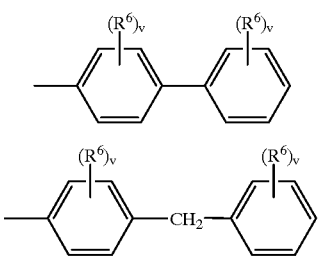

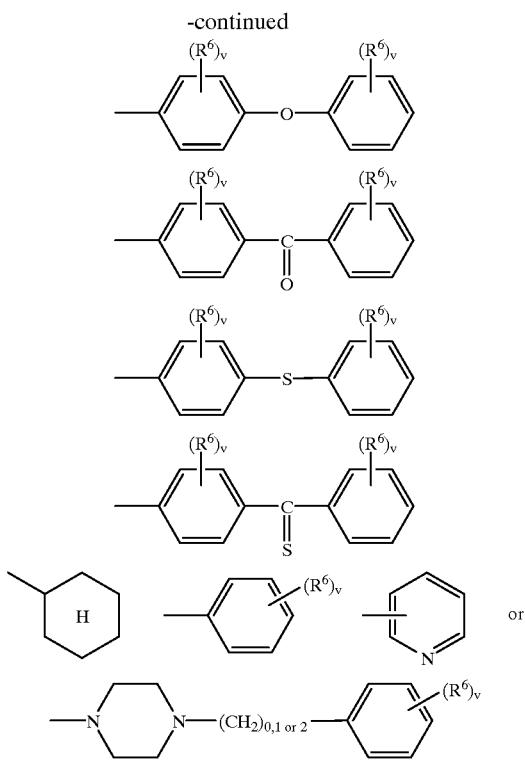

wherein $R^6$ is $(C_{1-4})$alkyl, hydroxy, —$N_3$, halogen (F, Cl, Br, I),
$CF_3$, $NO_2$ or $(C_{1-4})$alkoxy and v is 0, 1, 2 or 3,
or the salts thereof with physiologically acceptable acids or complexing agents.

Compounds of formula I form tautomers of formula II

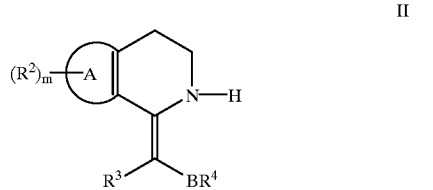

II

The tautomers can be separated by known methods e.g. by column chromatography or selective reduction ($NaBH_4$ or catalytic reduction).

The compounds of formula II may occur in cis- and/or trans-form:

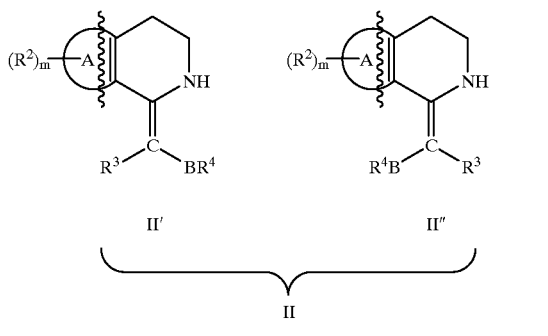

If the structure of a compound is not expressly stated, the mention of formula I should be taken as including structure II as well.

In the definitions used in the text the radicals and groups may be identical or different, i.e. if one of the above-mentioned substituents occurs several times in a particular molecule, the meaning can be selected freely within the scope of the definitions provided.

The term alkyl means $C_{1-6}$-alkyl and $C_{1-4}$-alkyl radicals which may be substituted or, as alkyl radicals, are part of a functional group such as alkoxy or alkylthio. The alkyl radicals include methyl, ethyl, n-propyl, isopropyl, n-butyl, sec.-butyl, isobutyl and tert.-butyl radicals as well as the various isomeric pentyl and hexyl radicals, such as e.g. isopentyl, neopentyl, n-pentyl and n-hexyl radical.

Halogens are fluorine, chlorine, bromine and iodine, preferably fluorine, chlorine and bromine and to a lesser extent iodine.

$C_{3-7}$-cycloalkyl denotes cyclopropane, cyclobutane, cyclopentane, cyclohexane and cycloheptane.

$C_{3-6}$-alkynes are the isomeric hexynes, pentynes, butynes and propynes, propargyl being preferred.

$C_{3-6}$-alkenes are the isomeric hexenes, pentenes, butenes and propenes, allyl being preferred.

A preferred aspect of the invention consists of compounds of general formula I wherein A denotes benzo; m is 2 (whilst the two $R^2$s are preferably in positions 6 and 7) and the substituents $R^2$ independently of one another represent hydroxy, $(C_{1-4})$alkoxy, benzyloxy, halogen (F, Cl, Br, I) or $(C_{1-4})$alkyl, or two adjacent substituents $R^2$ may together represent —O—$CH_2$—O;

B denotes the group —O—, —S— or —$CHR^5$—, wherein $R^5$ is hydrogen, methyl, phenyl or benzyl;

$R^3$ is 2- or 3-thienyl, $(C_{4-7})$cycloalkyl, or

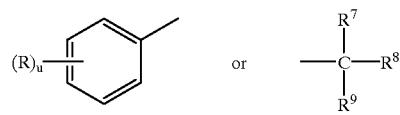

wherein
R is $(C_{1-4})$alkyl, halogen, (F, Cl, Br, I), $CF_3$ or $(C_{1-4})$alkoxy,
u is 0, 1, 2 or 3, and
$R^7$, $R^8$ and $R^9$ independently of one another may represent methyl, ethyl, propyl, phenyl or benzyl, but not more than 2 of the substituents may simultaneously represent phenyl or benzyl;
$R^4$ denotes
(a) branched or unbranched $C_{3-6}$-alkenyl which may be substituted by phenyl or
(b) branched or unbranched $C_{3-6}$-alkynyl which may be substituted by phenyl, or
(c) branched or unbranched $C_{1-13}$-alkyl, wherein the alkyl may be substituted by
thienyl,
adamantyl,
cyclohexyl,
phenoxy,
benzyloxy or
phenyl
(whilst this phenyl or the phenyl contained in the phenoxy group or benzyloxy.group may be mono-, di- or trisubstituted by $(C_{1-4})$alkoxy, halogen (F, Cl, Br, I), $CF_3$, $N_3$, $NO_2$, $(C_{1-4})$ alkyl, or —C(O)—O—(CH$_2$)$_{1-3}$—CH$_3$ or by the bridge —O—CH$_2$—O—), or by 2 unsubstituted phenyl groups;

(d)

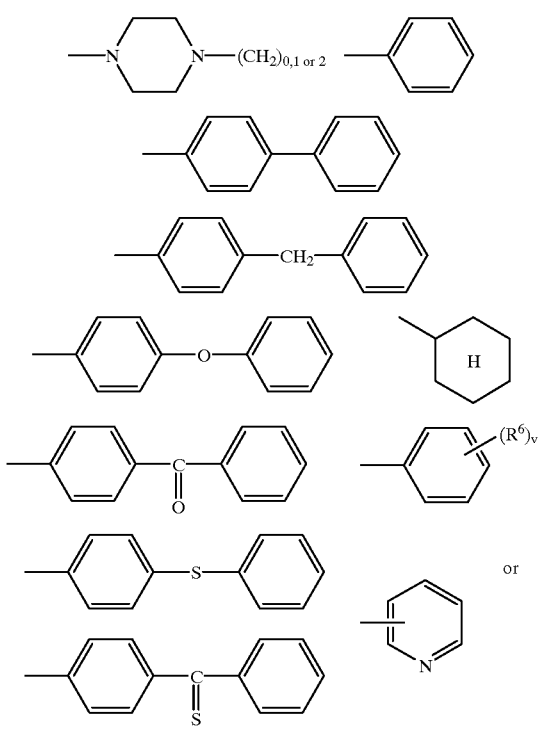

wherein R$^6$ denotes (C$_{1-4}$)alkyl, hydroxy, —N$_3$, halogen, (F, Cl, Br, I), CF$_3$, NO$_2$ or (C$_{1-4}$) alkoxy and v is 0, 1, 2 or 3, or the salts thereof with physiologically acceptable acids or complexing agents.

Of the compounds I wherein A is benzo, the preferred compounds are those wherein m is 2 and the two R$^2$S independently of each other represent methoxy, hydroxy, benzyloxy, methyl or chlorine or together represent —OCH$_2$O—, whilst the two R$^2$s are in positions 6 and 7, particularly those compounds wherein R$^2$ is methoxy, hydroxy, benzyloxy or methyl, and especially those wherein both R$^2$s are the same and represent hydroxy or methoxy.

Particular mention should be made of compounds I wherein R$^4$ has one of the following meanings:

a) vinyl, preferably substituted by phenyl;
b) unsubstituted C$_{4-9}$-alkyl which, if it is branched, contains methyl as a side chain or chains;
c) substituted C$_{1-4}$-alkyl (preferably C$_{2-3}$-alkyl) which, if it is branched, contains a methyl group as side chain,
  whilst the alkyl may be substituted by one or 2 phenyl groups,
    phenoxy
    benzyloxy
    thienyl (preferably 3-thienyl)
    cyclohexyl or
    1- or 2-adamantyl,
  whilst if the alkyl is substituted by a phenyl group or by phenoxy or benzyloxy, the appropriate phenyl group may be substituted by
    methyl,
    methoxy (1 to 3 methoxy groups),
    Cl, Br, CF$_3$,
    NO$_2$ or
    C(O)O(CH$_2$)$_3$CH$_3$ d)

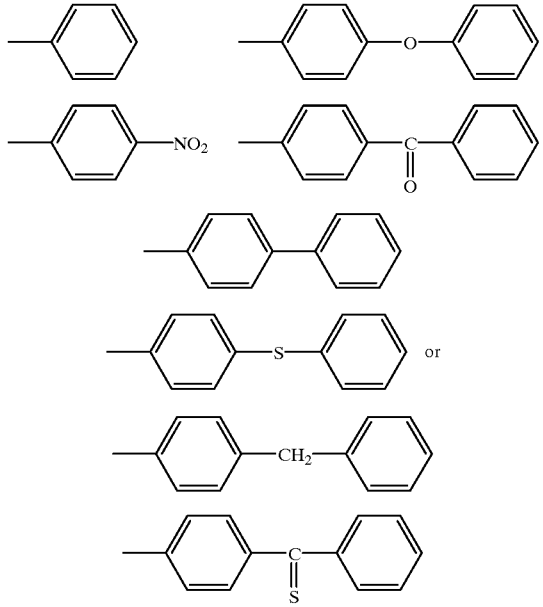

particularly those wherein R$^4$ has one of the following meanings:

a) R$^4$ denotes (C$_{4-7}$)alkyl;
b) substituted alkyl having 1 to 4 (preferably 2 or 3) carbon atoms which, if it is branched, contains a methyl group as side chain,
  whilst the alkyl may be substituted by one or 2 phenyl groups,
    phenoxy,
    benzyloxy
    thienyl (preferably 3-thienyl) or
    cyclohexyl,
  whilst if the alkyl is substituted by phenoxy or benzyloxy or preferably a phenyl group the relevant phenyl group may be substituted by
    methoxy (1 to 3 methoxy groups),
    Cl, Br, CF$_3$,
    NO$_2$ or
    C(O)O(CH$_2$)$_3$CH$_3$;

c)

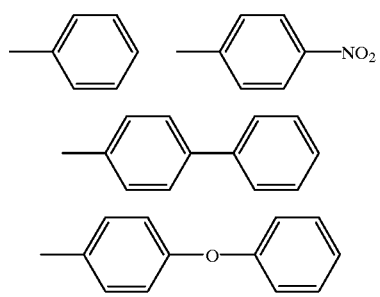

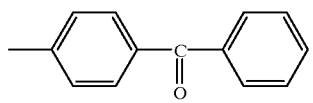

Particular mention should also be made of compounds (I) wherein B is O, S, $CH_2$ or $C(CH_3)H$, preferably those wherein B is O.

Special mention should also be made of compounds wherein $R^3$ represents phenyl (which may be mono-, di- or trisubstituted by methoxy, halogen or $CF_9$), cyclohexyl, thienyl or tert.butyl, especially those compounds wherein $R^3$ is phenyl, methoxyphenyl, Cl-benzyl, di-Cl-benzyl or cyclohexyl. Also worth mentioning are those compounds wherein $R^3$ is thienyl (preferably 3-thienyl) or tert.butyl.

Emphasis should also be placed on those compounds wherein A is benzo which is substituted in positions 6 and 7, wherein the two substituents $R^2$ independently of each other represent methoxy, benzyloxy, hydroxy, methyl or chlorine, particularly wherein $R^2$ in position 6 represents methoxy, hydroxy or benzyloxy and $R^2$ in position 7 represents methoxy or methyl, preferably wherein A is the 6,7-dimethoxybenzo group.

Special mention should be made of compounds wherein $R^4$ has one of the following meanings:

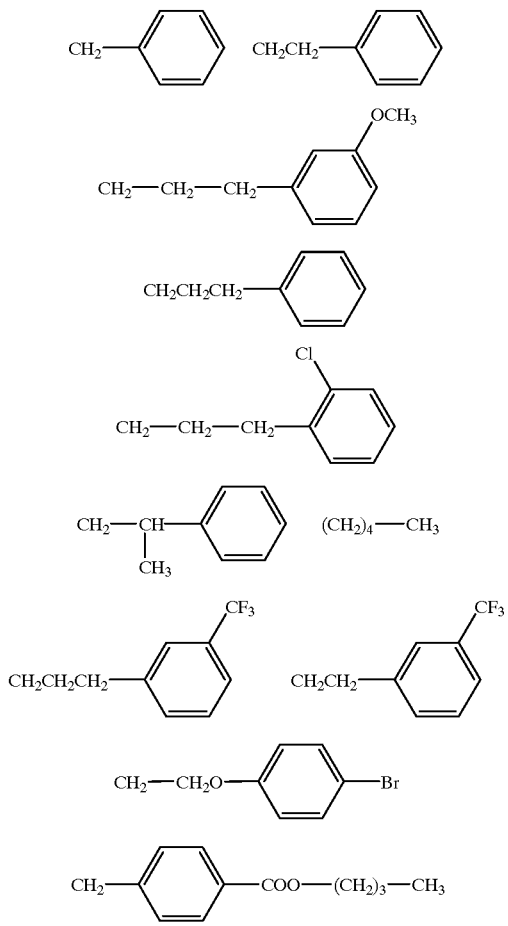

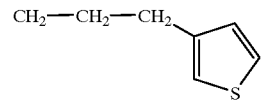

particularly those wherein B is O or $CH_2$ and A is defined as hereinbefore and is preferably 6,7-dimethoxybenzo. Within this group of compounds, those wherein $R^3$ is tert.butyl, thienyl or preferably phenyl or cyclohexyl are preferred.

The compounds of formula I may be prepared by methods known per se, preferably analogously to the method described in German Patent Application P 37 18 570.5, EP 358 957, EP 37 934, EP 251 794 and EP 288 048.

In the presence of a condensing agent, a compound of general formula IV

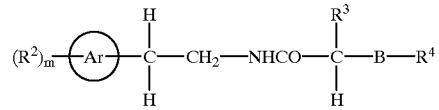

wherein $R^2$, $R^3$, $R^4$ and m are as hereinbefore defined and Ar represents phenyl, indolyl or 2- or 3-thienyl, may be cyclised to form the corresponding compounds.

Suitable condensing agents for this process are strong Lewis acids such as phosphorusoxychloride, phosphoruspentachloride, phosphorustrichloride, phosphoruspentoxide, titanium tetrachloride, boron trifluoride, tin tetrachloride, as well as organic acids such as polyphosphoric acid, sulphuric acid, fluorosulphonic acid and hydrofluoric acid, or mixtures of condensing agents such as a mixture of phosphorusoxychloride and phosphoruspentachloride, or a mixture of phosphoruspentoxide and $(C_{1-4})$alkylsulphonic acid, e.g. with a $P_2O_5$— content of about 10% by weight.

The cyclisation may be carried out in the presence or absence of a solvent. Any inert solvents are suitable provided that they have sufficient solubility for the reactants and a high enough boiling point, e.g. benzene, alkylbenzenes (e.g. toluene, xylene), chlorobenzenes, chloroform, acetonitrile and decaline. According to a preferred embodiment of the process the condensing agent used is phosphorusoxychloride in admixture with acetonitrile or a mixture of $(C_{1-4})$alkylsulphonic acid and phosphoruspentoxide, without the addition of solvents.

Preferably, the cyclisation is carried out with phosphorusoxychloride/acetonitrile or in difficult cases with a mixture of phosphoruspentoxide and $C_{1-4}$-alkylsulphonic acid (preferably methanesulphonic acid). The reaction can be carried out in a wide temperature range, preferably with heating to 50° C. up to the boiling point of the reaction mixture.

The length of reaction required will range from 2 to 15 hours depending on the starting compound IV used.

Starting compounds:

The ethers of general formula IV may be obtained in accordance with the conventional methods described in the literature. It is preferred to use the "mesylate and bromide method", particularly the mesylate method. With the preferred process it should be noted that the usual base must not be added during the reaction, so as to avoid the formation of undesirable non-ethereal by-products.

The thioethers of general formula IV may be obtained in accordance with the conventional methods described in the literature. The "mesylate method" is preferred: converting a mercaptan with the mesylate of N-(2-(3,4-dimethoxyphenyl)ethyl)-mandelic acid amide in solvent-free and base-free medium at 100° C.

The alkanes of general formula IV are obtained by reacting the 2-phenylalkylcarboxylic acids with 2-(3,4-dimethoxyphenylethylamine to obtain the open-ringed amides (preferably using the carbonyldiimidazole method).

The compounds of formula I are bases and can be converted in the usual way with inorganic or organic acids and salts and complex-forming agents into any desired physiologically acceptable adducts (salts).

Acids suitable for salt formation include for example hydrochloric, hydrobromic, hydriodic, hydrofluoric, sulphuric, phosphoric, nitric, acetic, propionic, butyric, caproic, valeric, oxalic, malonic, succinic, maleic, fumaric, lactic, tartaric, citric, malic, benzoic, p-hydroxybenzoic, phthalic, cinnamic, salicylic, ascorbic, methanesulphonic acid and the like.

The compounds may be administered by oral, parenteral or topical route. The desired therapeutic dose depends on the indication and formulation used and can be determined experimentally. Suitable forms include, for example, tablets, capsules, suppositories, solutions, syrups, emulsions, aerosols or dispersible powders. Tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release, such as carboxypolymethylene, carboxymethylcellulose, cellulose acetate phthalate or polyvinylacetate. The tablets may also consist of several layers.

Coated tablets may be produced analogously by coating cores made in the same way as the tablets with substances conventionally used for tablet coatings, e.g. collidone or shellack, gum arabic, talc, titanium dioxide or sugar. In order to obtain delayed release or avoid incompatibilities, the core may also consist of several layers. Similarly, the tablet coating may consist of several layers to achieve delayed release, whilst the excipients mentioned for the tablets may be used.

Syrups containing the active substances or combinations of active substances according to the invention may additionally contain a sweetener such as saccharin, cyclamate, glycerol or sugar as well as a flavour enhancer, e.g. a flavouring such as vanilla or orange extract. They may also contain suspension adjuvants or thickeners such as sodium carboxymethylcellulose, wetting agents, e.g. condensation products of fatty alcohols with ethylene oxide or preservatives such as p-hydroxybenzoates.

Injectable solutions are produced in the usual way, e.g. by adding preservatives such as p-hydroxybenzoates or stabilisers such as alkali metal salts of ethylene diamine tetraacetic acid, and are then transferred into injection vials or ampoules.

Capsules containing one or more active substances or combinations of active substances may be prepared for example by mixing the active substances with inert carriers such as lactose or sorbitol and encapsulating them in gelatine capsules.

Suitable suppositories may be produced for example by mixing with carriers provided for this purpose, such as neutral fats or polyethyleneglycol or derivatives thereof.

The compounds may be administered both enterally and parenterally. A proposed dose for oral use is 0.1 to 500 mg of active substance per dose and from 0.05 to 150 mg per dose for intravenous administration. The desired therapeutic dose depends on the indication and formulation used and can be determined experimentally.

The pharmaceutical compositions are suitable for oral or parenteral and possibly topical application. The chief formulations used are plain or coated tablets, ampoules and syrups. The single dose using these formulations is between 1.0 and 200 mg, preferably 20 to 50 mg per 75 kg of body weight. Generally, 1 to 3 single doses are required per day, depending on the gravity of the case.

The following Examples serve to illustrate the invention:

EXAMPLE 1

O-(3-Phenylpropyl)-phenylacetic acid

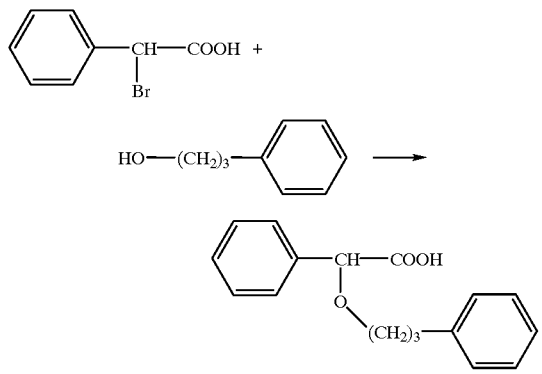

7.8 g (0.2 mol) of potassium are dissolved in 136 g (1 Mol) of 3-phenyl-1-propanol by heating to 100° and after cooling to ambient temperature a solution of 21.5 g (0.1 Mol) of α-bromophenylacetic acid in 20 ml of 3-phenyl-1-propanol is added dropwise.

After 2½ hours heating to 110° C., 500 ml of diethylether are added at ambient temperature and the solution is extracted 3 times with 100 ml of water. The combined aqueous extracts are acidified with 30 ml of 4N HCl whilst cooling with ice; the oil precipitated is taken up in ether, washed with water and dried over MgSO$_4$. After the solvent has been distilled off, 23.4 g (86.6% of theory) of the desired carboxylic acid ether are left as an oily residue which can be used for the following reaction without any further purification.

N-[2-(3,4-Dimethoxyphenyl)ethyl]-O-(3-phenylpropyl)-phenylacetic acid amide

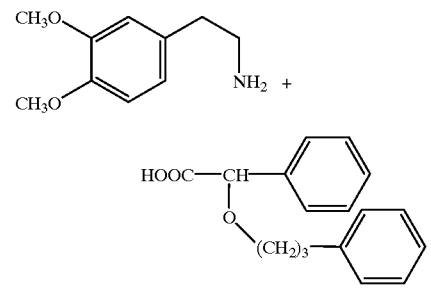

-continued

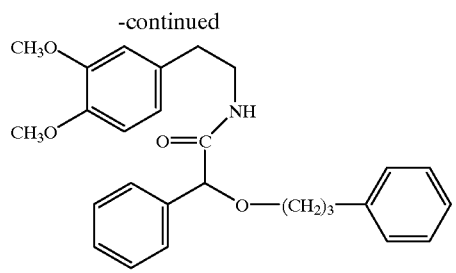

30.3 g (112 mmol) of O-(3-phenylpropyl)-phenylacetic acid are dissolved in 250 ml of absolute tetrahydrofuran, combined with 18.14 g (112 mmol) of carbonyldiimidazole and stirred for 2 hours at ambient temperature. Whilst cooling with ice, 20.27 g (112 mmol) of 2-(3,4-dimethoxyphenyl)-ethylamine in 50 ml of absolute tetrahydrofuran are added dropwise to this reaction solution and the resulting mixture is stirred for a further 15 hours at ambient temperature. Then the solvent is distilled off in vacuo, the residue is dissolved in 250 ml of ethyl acetate, washed 3 times with 100 ml of 1N HCl, twice with 75 ml of saturated NaHCO$_3$ solution and twice with 50 ml of saturated NaCl solution. The ethyl acetate solution is dried over MgSO$_4$ and evaporated down in vacuo.

The oily reaction product 44.28 g (91.3% of theory) can be processed without any further purification.

Alternative Embodiment

N-[2-(3,4-Dimethoxyphenyl)ethyl]-mandelic acid amide

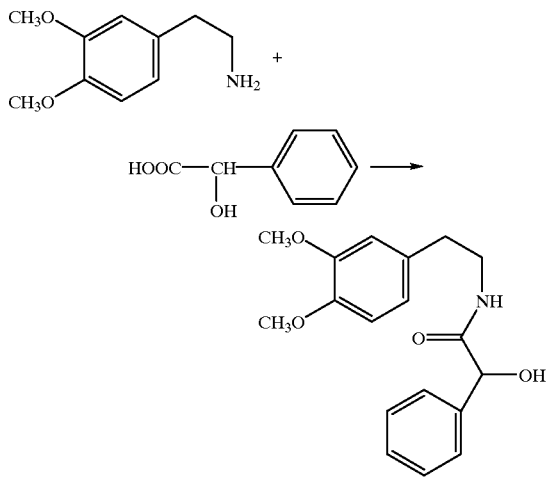

33.2 g (0.2 Mol) of methyl mandelate and 72 g (0.4 Mol) of 2-(3,4-dimethoxyphenyl)-ethylamine are heated to 160–165° C. under an N$_2$ atmosphere with stirring, for 5 hours using a descending condenser (to remove the methanol released). The cooled residue is dissolved in 300 ml of ethyl acetate, washed twice with 100 ml of 2N HCl, once with saturated NaHCO$_3$ solution and saturated NaCl solution, dried over MgSO$_4$ and distilled off from the solvent.

The crystalline residue is dissolved in 200 ml of ethyl acetate and the reaction product is precipitated with 160 ml of n-hexane.

Yield: 51.2 g (80.95% of theory), m.p.: 89–91°.

N-[2-(3,4-Dimethoxyphenyl)ethyl]-O-mesylmandelic acid amide

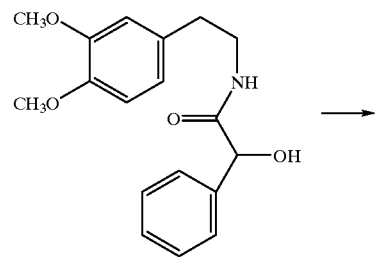

To a solution of 19.6 g (62.2 mmol) of N-[2-(3,4-dimethoxyphenyl)ethyl]-mandelic acid amide in 60 ml of absolute pyridine are added dropwise, with stirring and cooling, 7.8 (69 mmol) of methanesulphonic acid chloride, the reaction solution being maintained at −15 to −5°. After 5 hours' stirring at ambient temperature, 200 g of ice are added and the mixture is acidified with 180 ml of 4N HCl, whilst cooling with ice. The acid solution is extracted twice with 400 ml of ethyl acetate and the organic phase is washed twice with 50 ml of H$_2$O and twice with saturated NaCl solution, dried over MgSO$_4$ and the solvent is distilled off in vacuo. The crystalline residue is re-precipitated with 100 ml of ethyl acetate and 50 ml of n-heptane and 16.3 g (66.6% of theory) of the reaction product are obtained, m.p. 89–90° C.

N-[2-(3,4-Dimethoxyphenyl)ethyl]-O-(3-phenylpropyl)-phenylacetic acid amide

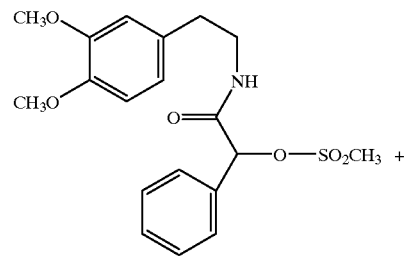

-continued

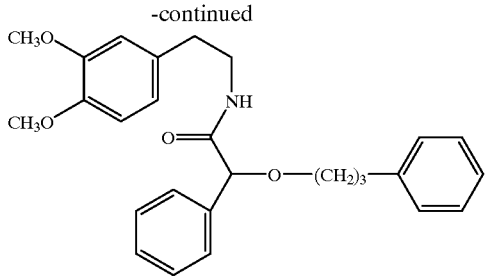

1.95 g (5 mmol) of N-[2-(3,4-dimethoxyphenyl)ethyl]-O-mesylmandelic acid amide are dissolved in 3.4 g (25 mmol) of 3-phenyl-1-propanol and heated to 100° C. for 30 minutes with stirring. After cooling to ambient temperature the reaction product is dissolved in 100 ml of ethyl acetate, washed twice with saturated $NaHCO_3$ solution and once with NaCl solution, dried over $MgSO_4$ and the solvent is distilled off in vacuo.

The oily reaction product is purified by chromatography over a silica gel column using ethyl acetate/n-heptane 1:1 and 1.54 g (71.5% of theory) of the desired ether are obtained in the form of an oil.

(R,S)-(3,4-Dihydro-6,7-dimethoxyisoquinolin-1-yl)-2-phenyl-2-(3-phenylpropyl)-ether

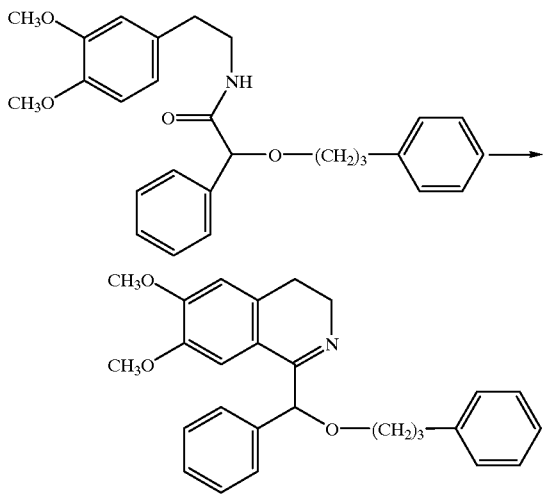

A solution of 44.28 g (102.3 mmol) of N-[2-(3,4-dimethoxyphenyl)ethyl]-O-(3-phenylpropyl)phenylacetic acid amide and 46.93 g (307 mmol) of phosphorusoxychloride in 300 ml of acetonitrile is refluxed for 1 hour in an $N_2$ atmosphere. After cooling to room temperature the reaction mixture is dissolved in 1 litre of ethyl acetate, washed twice with 150 ml of ice water, 3 times with 150 ml of saturated $NaHCO_3$ solution and twice with 100 ml of saturated NaCl solution, dried over $MgSO_4$ and the solvent is distilled off in vacuo. The residue is dissolved in 110 ml of acetone and acidified with ethereal HCl, with stirring and cooling with ice, whereupon 17.6 g (38.68% of theory) of the desired reaction product crystallise out in the form of the hydrochloride; m.p.: 176–178° C.

EXAMPLE 2

N-[2-(3,4-Dimethoxyphenyl)ethyl]-S-(3-phenylpropyl)-phenylacetic acid amide

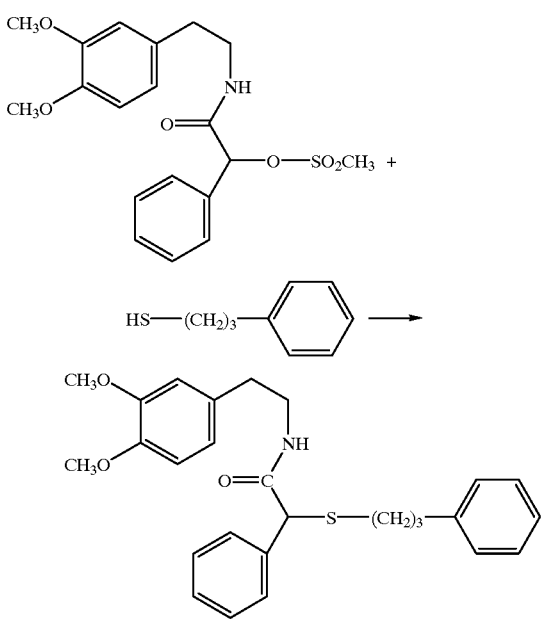

3.93 g (10 mmol) of N-[2-(3,4-dimethoxyphenyl)ethyl]-O-mesylmandelic acid amide and 4.56 g (30 mmol) of 3-phenyl-n-propylmercaptan are heated to 100° C. for 30 minutes, with stirring. The cooled reaction product is dissolved in 100 ml of ethyl acetate, washed twice with 20 ml of saturated $NaHCO_3$ solution and once with saturated NaCl solution. After drying over $MgSO_4$ the solvent is distilled off in vacuo. The oily residue is purified by chromatography over a silica gel column using ethyl acetate/n-heptane 1:1 as eluant.

Yield: 2.55 g (56.8% of theory).

(R,S)-(3,4-Dihydro-6,7-dimethoxyisoquinolin-1-yl)-2-phenyl-2-(3-phenylpropyl)-thioether

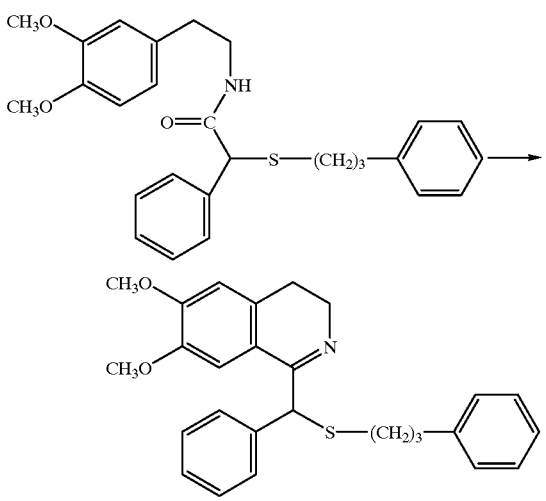

2.55 g (5.67 mmol) of N-[2-(3,4-dimethoxyphenyl)ethyl]-S-(3-phenylpropyl)phenylacetic acid amide and 2.6 g (17 mmol) of phosphorusoxychloride are heated to 100° in 35 ml of acetonitrile for 1.5 hours under an $N_2$ atmosphere, with stirring. The reaction solution is combined with 125 ml of ethyl acetate at ambient temperature, washed 3 times with 25 ml of ice water, 3 times with 25 ml of saturated $NaHCO_3$ solution and once with saturated NaCl solution and dried over $MgSO_4$.

After the organic phase has been distilled off in vacuo the oily residue is purified over a silica gel column with ethyl acetate as eluant and 1.18 g of the desired reaction product are obtained in amorphous form.

EXAMPLE 3

N-[2-(3,4-Dimethoxyphenyl)ethyl]-2,5-diphenylpentane-carboxylic acid amide

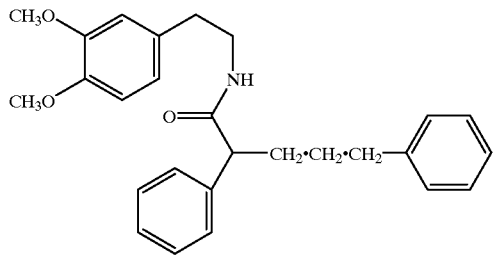

A solution of 3.0 g (11.8 mmol) of 2,5-diphenylpentane carboxylic acid and 1.91 9 (11.8 mmol) of carbonyldiimidazole is stirred at ambient temperature for one hour and then mixed with a solution of 2.13 g (11.8 mmol) of 2-(3,4-dimethylethoxyphenyl)ethylamine in 20 ml of tetrahydrofuran, stirred overnight at ambient temperature and, after the solvent has been distilled off, the residue is dissolved in ethyl acetate. The organic phase is washed twice with 15 ml of 1N HCl, twice with 20 ml of saturated $NaHCO_3$ solution and then with a saturated NaCl solution. After drying over $MgSO_4$ and distilling off the solvent, 4.9 g (100% of theory) of the desired end product are left, and this end product is further processed in the form of an oil without any more purification.

(R,S)-(3,4-Dihydro-6,7-dimethoxyisoquinolin-1-yl)-1,4-diphenylbutane

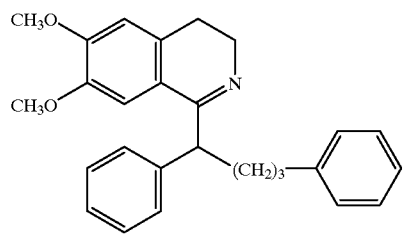

A solution of 4.9 g (11.75 mmol) of N-[2-(3,4-dimethoxyphenyl)ethyl]-2,5-diphenylpentanecarboxylic acid amide and 5.39 g (35.2 mmol) of phosphorusoxychloride in 40 ml of absolute acetonitrile is refluxed for 1.5 hours under an $N_2$ atmosphere, with stirring. The reaction solution is diluted with 150 ml of ethyl acetate and washed successively twice with 40 ml of ice water, three times with 30 ml of saturated $NaHCO_3$ solution and with saturated NaCl solution and the organic phase is dried over $MgSO_4$. After the solvent has been distilled off in vacuo, the oily residue is dissolved in acetone and acidified with ethereal hydrochloric acid.

The desired reaction product is obtained as an amorphous solid substance in the form of the hydrochloride salt.

Yield: 2.6 g (50.8% of theory)

The following Tables list examples of compounds according to the invention. These compounds may be prepared analogously to the processes described hereinbefore.

TABLE 1

| No. | $R_1$ | $R_2$ | $R_3$ | $R_4$ | Mp. °C. | Salt form |
|---|---|---|---|---|---|---|
| 1 | $OCH_3$ | $OCH_3$ | $C_6H_5$ | $C_6H_5$ | amorph | OX |
| 2 | $OCH_3$ | $OCH_3$ | $C_6H_5$ | $CH_2C_6H_5$ | 142–145 | OX |
| 3 | $OCH_3$ | $OCH_3$ | $C_6H_5$ | $CH_2CH_2C_6H_5$ | 165–168 | CL |
| 4 | $OCH_3$ | $OCH_3$ | $C_6H_5$ | $CH_2CH_2CH_2C_6H_5$ | 176–178 | CL |
| 5 | $OCH_3$ | $OCH_3$ | $C_6H_5$ | $CH_2CH_2CH_2CH_2C_6H_5$ | 57–60 | OX |
| 6 | $OCH_3$ | $OCH_3$ | $C_6H_5$ | $CH_2CH(CH_3)C_6H_5$ | 112–114 | OX |
| 7 | $OCH_3$ | $OCH_3$ | $C_6H_5$ | $CH_2CH_2CH(CH_3)C_6H_5$ | | |

TABLE 1-continued

Structure:

R₁—[benzene ring fused to]—N=C(R₃)(CH(—O—R₄))—... 
(6,7-disubstituted 3,4-dihydroisoquinoline with 1-position bearing CH(R₃)(OR₄))

| No. | R₁ | R₂ | R₃ | R₄ | Mp. °C. | Salt form |
|---|---|---|---|---|---|---|
| 8 | OCH₃ | OCH₃ | C₆H₅ | —CH₂—CH₂—CH₃ | | |
| 9 | OCH₃ | OCH₃ | C₆H₅ | —CH₂—CH₂—CH₂—CH₃ | | |
| 10 | OCH₃ | OCH₃ | C₆H₅ | —CH₂—CH₂—(2-OCH₃-C₆H₄) | 123–126 | CL |
| 11 | OCH₃ | OCH₃ | C₆H₅ | —CH₂—CH₂—(3-OCH₃-C₆H₄) | 70–80 | OX |
| 12 | OCH₃ | OCH₃ | C₆H₅ | —CH₂—CH₂—(4-OCH₃-C₆H₄) | amorph | CL |
| 13 | OCH₃ | OCH₃ | C₆H₅ | —CH₂—CH₂—(2,3,4-tri-OCH₃-C₆H₂) | amorph | OX |

TABLE 1-continued
| No. | $R_1$ | $R_2$ | $R_3$ | $R_4$ | Mp. °C. | Salt form |
|---|---|---|---|---|---|---|
| 14 | OCH$_3$ | OCH$_3$ | 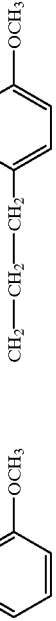 |  | amorph | OX |
| 15 | OCH$_3$ | OCH$_3$ |  |  | amorph | OX |
| 16 | OCH$_3$ | OCH$_3$ | C$_6$H$_5$ |  | | |
| 17 | OCH$_3$ | OCH$_3$ | C$_6$H$_5$ | 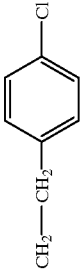 | | |
| 18 | OCH$_3$ | OCH$_3$ | C$_6$H$_5$ |  | 141–143 | OX |
| 19 | OCH$_3$ | OCH$_3$ | C$_6$H$_5$ |  | 143–145 | MA |

TABLE 1-continued

![structure: R1, R2 substituted 3,4-dihydroisoquinoline with C(R3)(OR4) at position 1]

| No. | $R_1$ | $R_2$ | $R_3$ | $R_4$ | Mp. °C. | Salt form |
|---|---|---|---|---|---|---|
| 21 | $OCH_3$ | $OCH_3$ | 4-Cl-$C_6H_4$ | $CH_2CH_2$-$C_6H_5$ | 139–142 | OX |
| 22 | $OCH_3$ | $OCH_3$ | 3,5-Cl$_2$-$C_6H_3$ | $CH_2CH_2$-$C_6H_5$ | 159–163 | OX |
| 23 | $OCH_3$ | $OCH_3$ | $C_6H_5$ | $CH_2CH_2$-(2-$CF_3$-$C_6H_4$) | | |
| 24 | $OCH_3$ | $OCH_3$ | $C_6H_5$ | $CH_2CH_2$-(3-$CF_3$-$C_6H_4$) | 108–110 | CL |
| 25 | $OCH_3$ | $OCH_3$ | $C_6H_5$ | $CH_2CH_2$-(4-$CF_3$-$C_6H_4$) | | |
| 26 | $OCH_3$ | $OCH_3$ | $C_6H_5$ | $CH_2CH_2$-(3-$CF_3$-$C_6H_4$) | amorph | OX |

TABLE 1-continued
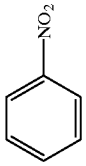
| No. | $R_1$ | $R_2$ | $R_3$ | $R_4$ | Mp. °C. | Salt form |
|---|---|---|---|---|---|---|
| 27 | OCH$_3$ | OCH$_3$ | C$_6$H$_5$ | | 138–140 | OX |
| 28 | OCH$_3$ | OCH$_3$ | C$_6$H$_5$ | CH$_2$-(2-NO$_2$-C$_6$H$_4$) | | |
| 29 | OCH$_3$ | OCH$_3$ | C$_6$H$_5$ | CH$_2$-(3-NO$_2$-C$_6$H$_4$) | 157–159 | MA |
| 30 | OCH$_3$ | OCH$_3$ | C$_6$H$_5$ | CH$_2$-(4-NO$_2$-C$_6$H$_4$) | | |
| 31 | OCH$_3$ | OCH$_3$ | C$_6$H$_5$ | CH$_2$CH$_2$-(3-NO$_2$-C$_6$H$_4$) | 180–182 | CL |
| 32 | OCH$_3$ | OCH$_3$ | C$_6$H$_5$ | CH$_2$CH$_2$-O-C$_6$H$_5$ | amorph | CL |

TABLE 1-continued
| No. | R₁ | R₂ | R₃ | R₄ | Mp. °C. | Salt form |
|---|---|---|---|---|---|---|
| 33 | OCH₃ | OCH₃ | C₆H₅ |  CH₂—CH₂—O—CH₂ | amorph | OX |
| 34 | OCH₃ | OCH₃ | C₆H₅ |  | | |
| 35 | OCH₃ | OCH₃ | C₆H₅ |  | | |
| 36 | OCH₃ | OCH₃ | C₆H₅ |  | 120–122 | MA |
| 37 | OCH₃ | OCH₃ | C₆H₅ |  | 80–100 (Decomposition) | OX |
| 38 | OCH₃ | OCH₃ | C₆H₅ | | | |

TABLE 1-continued
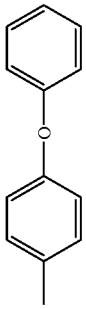
| No. | $R_1$ | $R_2$ | $R_3$ | $R_4$ | Mp. °C. | Salt form |
|---|---|---|---|---|---|---|
| 39 | $OCH_3$ | $OCH_3$ | $C_6H_5$ | 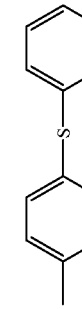 | 50–75 (Decomposition) | OX |
| 40 | $OCH_3$ | $OCH_3$ | $C_6H_5$ | 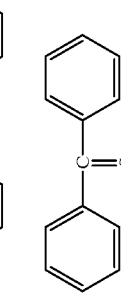 | | |
| 42 | $OCH_3$ | $OCH_3$ | $C_6H_5$ | 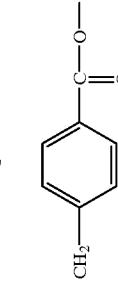 | | |
| 43 | $OCH_3$ | $OCH_3$ | $C_6H_5$ | 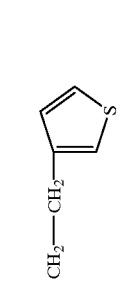 | amorph | OX |
| 44 | $OCH_3$ | $OCH_3$ | $C_6H_5$ |  | amorph | OX |
| 45 | $OCH_3$ | $OCH_3$ | $C_6H_5$ | 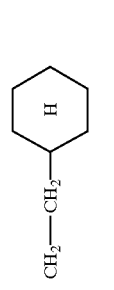 | 60–70 (Decomposition) | OX |
| 46 | $OCH_3$ | $OCH_3$ | $C_6H_5$ |  | 124–17 | OX |

TABLE 1-continued

Structure: R₁, R₂ on benzene ring fused to tetrahydroisoquinoline with C(R₃)(OR₄) at position 1

| No. | R₁ | R₂ | R₃ | R₄ | Mp. °C. | Salt form |
|-----|------|------|------|------|---------|-----------|
| 47 | OCH₃ | OCH₃ | C₆H₅ | CH₂—CH₂—C₆H₁₁ (cyclohexyl) | 145–147 | OX |
| 48 | OCH₃ | OCH₃ | C₆H₁₁ (cyclohexyl) | CH₂—CH₂—C₆H₅ | 138–140 | OX |
| 50 | OCH₃ | OCH₃ | C₆H₅ | CH₂—CH₂—C₆H₅ | 65–80 (Decomposition) | OX |
| 51 | OCH₂—C₆H₅ | OCH₃ | C₆H₅ | CH₂—CH₂—C₆H₅ | amorph | OX |
| 52 | OCH₃ | OCH₃ | C₆H₅ | CH₂—CH₂—C₆H₅ | 75–120 (Decomposition) | OX |
| 53 | OCH₂—C₆H₅ | OCH₃ | C₆H₅ | CH₂—CH₂—C₆H₅ | amorph | OX |
| 54 | OCH₃ | OCH₃ | C₆H₅ | CH₂—CH₂—C₆H₅ | | OX |

TABLE 1-continued

Structure: R₁, R₂ on isoquinoline with N, CH(R₃)—O—R₄ substituent

| No. | R₁ | R₂ | R₃ | R₄ | Mp. °C. | Salt form |
|---|---|---|---|---|---|---|
| 55 | OCH₂—C₆H₅ | OCH₃ | C₆H₅ | —CH₂—CH₂—(phenyl) | | |
| 56 | OCH₃ | OCH₃ | 3-methylthienyl | —CH₂—CH₂—(phenyl) | | |
| 57 | OCH₃ | OCH₃ | 3-methylthienyl | —CH₂—CH₂—(phenyl) | | |
| 58 | OCH₃ | OCH₃ | C₆H₅ | —CH₂—CH₂—(phenyl)₂ | amorph | CL |
| 59 | OCH₃ | OCH₃ | C₆H₅ | CH₂CH₂CH₂CH₃ | 105–110 | OX |
| 60 | OCH₃ | OCH₃ | C₆H₅ | CH₂CH₂CH₂CH₂CH₃ | 82–85 | OX |
| 61 | OCH₃ | OCH₃ | C₆H₅ | CH₂CH₂CH₂CH₂CH₂CH₃ | 96–100 | OX |
| 62 | OCH₃ | OCH₃ | C₆H₅ | CH₂CH₂CH₂CH₂CH₂CH₂CH₃ | 60–65 | OX |
| 63 | OCH₃ | OCH₃ | C₆H₅ | CH₂CH₂CH₂CH₂CH₂CH₂CH₂CH₃ | | |
| 64 | OCH₃ | OCH₃ | C₆H₅ | CH₂—CH(CH₃)—CH₂—CH₃ | ~60 (decomposition) | OX |
| 65 | OCH₃ | OCH₃ | C₆H₅ | CH₂—CH₂—CH(CH₃)—CH₂—CH₃ | | |

TABLE 1-continued

| No. | $R_1$ | $R_2$ | $R_3$ | $R_4$ | Mp. °C. | Salt form |
|---|---|---|---|---|---|---|
| 66 | $OCH_3$ | $OCH_3$ | $C_6H_5$ | $CH_2-CH_2-CH_2-CH-CH_3$ <br> $\qquad\qquad\qquad\quad\;\;\;CH_3$ | | |
| 67 | $OCH_3$ | $OCH_3$ | $C_6H_5$ | $CH_3$ <br> $CH_3-C-CH_3$ <br> $CH_3$ | 150–152 | OX |
| 68 | $OCH_3$ | $OCH_3$ | $C_6H_5$ | $CH_3$ <br> $CH_2-C-CH_3$ <br> $CH_3$ | 105–110 | OX |
| 69 | $OCH_3$ | $OCH_3$ | $C_6H_5$ | $CH_3$ <br> $CH_2-CH_2-C-CH_3$ <br> $CH_3$ | | |
| 70 | $OCH_3$ | $OCH_3$ | $C_6H_5$ | $CH_2CH_2$-1-Adamantane | 155–158 | OX |
| 71 | $OCH_3$ | $OCH_3$ | $C_6H_5$ | $CH_2CH_2$-1-Adamantane | | |
| 72 | $OCH_3$ | $OCH_3$ | $C_6H_5$ | $CH_2CH_2CH_2$-1-Adamantane | | |
| 73 | $OCH_3$ | $OCH_3$ | $C_6H_5$ | $CH_2CH_2CH_2$-1-Adamantane | | |
| 74a | $OCH_3$ | $OCH_3$ | $C_6H_5$ | $(CH_2)_3$—C$_6$H$_4$—Cl (2-chloro) | 135–136 | OX |

TABLE 2

![structure: 3,4-dihydroisoquinoline with R1, R2 on benzene ring and CH(R3)-S-R4 at position 1]

| No. | R₁ | R₂ | R₃ | R₄ | Mp. °C | Salt form |
|-----|-----|-----|-----|-----|--------|-----------|
| 74 | OCH₃ | OCH₃ | C₆H₅ | —CH₂—CH₂—CH₂—C₆H₅ | | |
| 75 | OCH₃ | OCH₃ | C₆H₅ | —CH₂—CH(CH₃)—C₆H₅ | | |
| 76 | OCH₃ | OCH₃ | C₆H₅ | —CH₂—CH₂—(3-CF₃-C₆H₄) | | |
| 77 | OCH₃ | OCH₃ | C₆H₅ | —CH₂—CH₂—O—(4-Br-C₆H₄) | | |
| 78 | OCH₃ | OCH₃ | C₆H₅ | —CH₂—(4-COO—(CH₂)₃—CH₃)—C₆H₄ | | |
| 79 | OH | OCH₃ | C₆H₅ | —CH₂—CH₂—CH₂—C₆H₅ | | |
| 80 | OH | CH₃ | 4-methylthiophen-3-yl | —CH₂—CH₂—CH₂—C₆H₅ | | |
| 81 | OH | CH₃ | cyclohexyl | —CH₂—CH₂—C₆H₅ | | |
| 82 | OCH₃ | OCH₃ | 4-methylthiophen-3-yl | —CH₂—CH₂—CH₂—C₆H₅ | | |
| 83 | OCH₃ | OCH₃ | 4-methylthiophen-3-yl | —CH₂—CH₂—CH₂—C₆H₅ | | |

TABLE 2-continued

[Structure: 3,4-dihydroisoquinoline with R₁, R₂ on benzene ring and CH(R₃)-S-R₄ at position 1]

| No. | R₁ | R₂ | R₃ | R₄ | Mp. °C. | Salt form |
|---|---|---|---|---|---|---|
| 85 | OH | Cl | 3-methylthiophene | -CH₂-CH₂-CH₂-(3-thienyl) | | |
| 86 | OCH₃ | OCH₃ | cyclohexyl-H | -CH₂-CH₂-CH₂-C₆H₅ | | |
| 87 | OH | CH₃ | C₆H₅ | -CH₂-CH₂-CH₂-C₆H₅ | | |

TABLE 3

[Structure: 3,4-dihydroisoquinoline with R₁, R₂ on benzene ring and CH(R₃)-B-R₄ at position 1]

| No. | R₁ | R₂ | R₃ | BR₄ | Mp. °C. | Salt form |
|---|---|---|---|---|---|---|
| 88 | OCH₃ | OCH₃ | C₆H₅ | -CH₂-CH₂-C₆H₅ | 190–192 | CL |
| 89 | OCH₃ | OCH₃ | C₆H₅ | -CH₂-CH₂-CH₂-C₆H₅ | amorph | CL |
| 90 | OCH₃ | OCH₃ | C₆H₅ | -CH₂-CH₂-CH₂-CH₂-C₆H₅ | 185–195 | CL |
| 91 | OCH₃ | OCH₃ | C₆H₅ | -CH₂-CH(CH₃)-C₆H₅ | | |
| 92 | OCH₃ | OCH₃ | C₆H₅ | -CH₂-CH₂-CH(CH₃)-C₆H₅ | | |

TABLE 3-continued structure: isoquinoline core with R1, R2 substituents at positions 6,7; position 1 has CH(R3)-B-R4

| No. | R₂ | R₂ | R₃ | BR₄ | Mp. °C. | Salt form |
|---|---|---|---|---|---|---|
| 93 | OCH₃ | OCH₃ | C₆H₅ | CH(CH₃)—CH₂—CH₂—C₆H₅ | | |
| 94 | OCH₃ | OCH₃ | C₆H₅ | CH₂—CH₂—CH₂—(3-CF₃-C₆H₄) | | |
| 95 | OCH₃ | OCH₃ | C₆H₅ | CH₂—CH₂—O—(4-Br-C₆H₄) | | |
| 96 | OCH₃ | OCH₃ | C₆H₅ | CH₂—CH₂—(4-COO(CH₂)₃CH₃-C₆H₄) | | |
| 97 | OCH₃ | OCH₃ | C₆H₅ | —CH₂—CH₂—CH₂—(3-thienyl) | | |
| 98 | OCH₃ | (4-methyl-3-thienyl) | | —CH₂—CH₂—CH₂—CH₂—C₆H₅ | | |
| 99 | OCH₃ | cyclohexyl | | —CH₂—CH₂—CH₂—CH₂—C₆H₅ | | |
| 100 | OCH₃ | cyclohexyl | | —CH₂—CH₂—CH₂—(3-thienyl) | | |
| 101 | OCH₃ | OCH₃ | t-Butyl | —CH₂—CH₂—CH₂—CH₂—C₆H₅ | | |
| 103 | OCH₃ | C₆H₅ | | CH₂—CH₂—CH₂—CH₂—C₆H₅ | | |
| 104 | OH | OCH₃ | (3-methyl-thienyl) | CH₂—CH₂—CH₂—CH₂—C₆H₅ | | |

TABLE 3-continued

| No. | R$_2$ | R$_2$ | R$_3$ | BR$_4$ | Mp. °C. | Salt form |
|---|---|---|---|---|---|---|
| 105 | OH | CH$_3$ | C$_6$H$_5$ | CH$_2$—CH$_2$—CH$_2$—(phenyl) | | |
| 106 | OH | CH$_3$ | 3-methylthienyl | CH$_2$—CH$_2$—CH$_2$—(phenyl) | | |
| 107 | OH | CH$_3$ | cyclohexyl | CH$_2$—CH$_2$—CH—(phenyl) | | |
| 108 | OH | CH$_3$ | C$_6$H$_5$ | CH$_2$—CH$_2$—CH$_2$—(thienyl) | | |
| 109 | OH | Cl | C$_6$H$_5$ | CH$_2$—CH$_2$—CH$_2$—(phenyl) | | |
| 110 | OH | Cl | 3-methylthienyl | CH$_2$—CH$_2$—CH$_2$—(phenyl) | | |
| 111 | OH | Cl | cyclohexyl | CH$_2$—CH$_2$—CH$_2$—(phenyl) | | |
| 112 | OH | Cl | C$_6$H$_5$ | CH$_2$—CH$_2$—CH$_2$—(thienyl) | | |
| 113 | OCH$_3$ | OCH$_3$ | t-Butyl | CH$_2$—CH$_2$—CH$_2$—(phenyl) | | |
| 114 | OCH$_3$ | OCH$_3$ | t-Butyl | CH$_2$—CH$_2$—CH$_2$—(thienyl) | | |
| 115 | OCH$_3$ | OCH$_3$ | 3-methylthienyl | CH$_2$—CH$_2$—CH$_2$—(thienyl) | | |

TABLE 3-continued

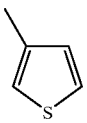

| No. | R₂ | R₂ | R₃ | BR₄ | Mp. °C. | Salt form |
|---|---|---|---|---|---|---|
| 116 | OH | OCH₃ | 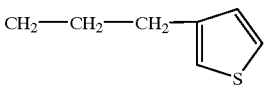 | 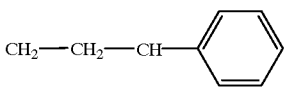 | | |
| 117 | OCH₃ | OCH₃ | C₆H₅ | $CH_2-CH_2-CH$ 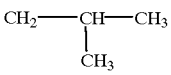 | amorph | CL |
| 118 | OCH₃ | OCH₃ | C₆H₅ | $CH_2.CH_2.CH_2.CH_2.CH_3$ | 105–110 | OX |
| 119 | OCH₃ | OCH₃ | C₆H₅ | $CH_2.CH.CH_2.CH_2.CH_2.CH_3$ | 90–93 | OX |
| 120 | OCH₃ | OCH₃ | C₆H₅ | $CH_2-(CH_2)_5-CH_3$ | 96–100 | |
| 121 | OCH₃ | OCH₃ | C₆H₅ | $CH_2-(CH_2)_6-CH_3$ | amorph | OX |
| 122 | OCH₃ | OCH₃ | C₆H₅ | $CH_2-(CH_2)_8-CH_3$ | 45–53 (decomposition) | OX |
| 123 | OCH₃ | OCH₃ | C₆H₅ | $CH_2.CH_2.CH_2$-1-Adamantane | | |
| 125 | OCH₃ | OCH₃ | C₆H₅ | $CH_2-(CH_2)_{10}-CH_3$ | amorph | OX |
| 126 | OCH₃ | OCH₃ | C₆H₅ | $CH_2-CH(CH_3)-CH_3$ | 178–180 | CL |
| 127 | OCH₃ | OCH₃ | C₆H₅ | $CH_2-CH_2-CH(CH_3)_2$ | 198–202 | Cl |
| 128 | OCH₃ | OCH₃ | C₆H₅ | $CH_2-CH_2-CH_3$ | 144–147 | OX |
| 129 | OCH₃ | OCH₃ | 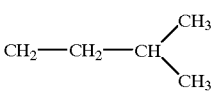 H | $CH_2-CH_2-$ | 121–124 | OX |

The present invention also relates to the use of these new compounds.

The compounds are valuable in the treatment of degenerative and necrotic diseases of the brain. It is also possible to provide preventative treatment for patients who are at risk from such diseases. The effect of the compounds is not based on an improvement in the blood flow through the tissues. The compounds are therefore suitable for a new kind of treatment of epilepsy and Alzheimer's disease and particularly for treating patients who have suffered a stroke or are at risk of suffering a stroke.

The present invention further relates to the use of the above compounds for preparing agents for the treatment of chronic inflammatory processes, ulcerative colitis and Crohn's disease and agents with an antiproliferative activity. The effect of the compounds can be explained by their inhibition of the unselective cation channels (UCC).

The pathophysiology of chronic bronchial asthma is based on inflammatory processes which are mediated by the activation of inflammatory cells. (BARNES, 1987; SEIFERT and SCHULTZ, 1991).

The receptor-regulated activation of inflammatory cells (e.g. neutrophilic granulocytes and mast cells or the permanent cell lines HL-60 (human leukemia) cells or sensitized RBL (rat basophilic lymphoma) cells, i.e. those charged with gammaglobulin E) is inhibited, irrespective of the nature of the stimulating agonists (e.g. endothelin, PAF, leukotrienes, chemotactical peptide fMLP or antigen against sensitized mast cells) by blockers of unselective cation channels (UCC) (RINK, 1990). Through these channels extracellular calcium, which is responsible for the persistence of receptor-mediated cell activations, enters the cells (PUTNEY, 1990). If this supply of calcium is interrupted this results in a blockade of the activation of inflammatory cells.

Conventional calcium antagonists of the dihydropyridine or phenylalkylamine type do not inhibit either UCCs or inflammatory processes (WELLS et al., 1986).

As a measurement of the cell activation or as a measurement of the inhibition thereof by UCC blockers, the kinetics of the cytoplasmic calcium ion concentration in fura-2-charged cells is quantified fluorometrically using the method described by GRYNKIEWICZ et al. (1985). This procedure has proved a reliable screening method, within the scope of the invention, for detecting UCC blockers.

So-called functional THAPSIGARGIN inhibition has proved suitable for the specific characterisation of blockers of the unselective cation channels. THAPSIGARGIN is a tumour promoter described by THASTRUP et al. (Proc. Natl. Acad. Sci. (USA), 87, 2466–2470, 1990) which selectively and irreversibly inhibits the $Ca^{2+}$-ATPase of intracellular $IP_3$-sensitive $Ca^{2+}$-stores. Consequently the $Ca^{2+}$-stores are rapidly depleted. As described by J. PUTNEY (Calcium, 11, 611–624, 1990) the depletion of these stores constitutes the physiological stimulation for opening up unselective cation channels in the cell membrane. The result of this is a massive influx of $Na^+$ and $Ca^{2+}$ into the cell. Because of these properties, Thapsigargin is suitable as an indirect stimulator for agonist- and $IP_3$-independent opening up of the unselective cation channels.

Within the scope of the present invention the Thapsigargin stimulation of unselective cation channels has been carried out successfully on HL 60 cells (human leukaemia cells), on hippocampal and cortical neurone cells and on RBL-cells (rat basophilic lymphoma cells) and in this way the existence of these channels in particular cell lines was demonstrated.

The cytoplasmic $Ca^{2+}$ concentration ($[Ca^{2+}]_i$) plays an important part in the cell proliferation and in tumour growth (for a summary see L. R. ZACHARSKI, Journal of Medicine 19: 145–177, 1988). In particular, the $Ca^{2+}$-influx into the cell stimulated by receptor activation with consecutive inositoltriphosphate-($IP_3$-)-mediation would appear to be of crucial importance for oncogenic cell proliferation (U. KIKKAWA and Y. NISHIZUKA, Ann. REV. CELL. BIOL. 2: 149–178, 1986). This mechanism also plays a part in the formation of metastases and in "Multi-Drug Resistance". (For a summary see the above-mentioned publication by L. R. ZACHARSKI, J. MED. 19: 145–177, 1980).

This hypothesis is supported by the fact that Thapsigargin, as an indirect stimulator of the unselective cation channels (UCC) not only leads to a $Ca^{2+}$-overload in the cell but is also a highly effective tumour promoter. (V. THASTRUP et al. Proceedings of the NATL. Acad. Sci: (USA) 87: 2466–2470, 1990). The blockade of the $Ca^{2+}$-influx by the UCC leads to normalisation of the intracellular Ca-ion concentration and hence to inhibition of tumour growth etc.

Conventional calcium antagonists do not inhibit these UCC. It has been found, surprisingly, that the compounds according to this invention inhibit the influx of calcium into the cell through the UCC.

As shown by S. H. MURCH et al. (Lancet 339: 381–385, Feb. 15, 1992) endothelin I plays an important pathophysiological role in inflammatory intestinal diseases such as ulcerative colitis and Crohn's disease. Using immunohistochemical methods it has been shown that patients with Crohn's disease in the region of the submucosa and patients with ulcerative colitis in the region of the lamina propria of the epithelium of the large intestine show significantly and greatly increased concentrations of endothelin I compared with healthy normal people. It is assumed that the local secretion of endothelin causes massive vasospasms with consecutive disseminated ischaemia with microinfarcts which are regarded as the actual cause of the above diseases. The vasospasmogenic effectiveness of endothelin is explained by a $Ca^{2+}$-overload of vascular myocytes. Endothelin primarily triggers an $IP_3$-mediated intracellular release of $Ca^{2+}$ which is followed by a massive transmembranal $Ca^{2+}$-entry through dihydropyridine-insensitive channels. (M. S. Simonson et al. Clin. Invest. Med. 14: 499–507, 1991; T. Masakai, J. Cardiovasc. Pharmacol. 13:Suppl. 5, S1-S4, 1989; D. W. Hay, R. J. Pharmacol. 100: 383–392, 1990). These channels are unselective cation channels which have also been briefly described as existing in cells of the large intestine mucosa. (Chr. Siemer and H. Gögelein, Europ. J. Physiol. 420: 319–328, 1992).

The endothelin-stimulated activation of fura-2-charged human leukaemia cells (HL 60 cells) has proved a suitable screening model for detecting functional endothelin antagonists. In conformity with G. GRYNKIEWICZ et al. (J. Biol. Chem. 260:3440–3450, 1985) the intracellular $Ca^{2+}$-concentration in the cytoplasm of HL 60 cells (suspensions) can be monitored by spectrofluorometry and quantified as a measurement of cell activation by endothelin. The stimulation was effected by adding 0.1 mM endothelin and could be inhibited in a dosage-dependent manner by means of the substances according to the invention.

The functional endothelin antagonism of the substances according to the invention is mediated through a blockade of the unselective cation channels. Consequently, detection of a functional Thapsigargin-antagonism on RBL-hm1 cells is also a suitable screening method for functional endothelin antagonists.

Carrying Out the Investigation:

For screening purposes, fura-2-charged adhesive RBL-hm 1 cells are stimulated with 0.1 μM Thapsigargin in a $Ca^{2+}$-free incubation medium. After 4 minutes, extracellular $Ca^{2+}$ is restored to a concentration of 1.5 mM and, using the fura-2-fluorescence, the excessive increase in the cytoplasmic $Ca^{2+}$-concentration caused by a massive transmembranal $Ca^{2+}$-entry through unselective cation channels is recorded.

This entry is to be inhibited solely by unselective cation channel blockers in a dosage-dependent manner. Neither conventional calcium antagonists nor specific blockers of agonists which stimulate the $IP_3$-turnover are able to inhibit the transmembranal $Ca^{2+}$-entry triggered indirectly by Thapsigargin. The compounds of the present invention are distinguished by their inhibition of UCC.

The fluorometric calcium measurement in the cytoplasm of individual adhering RBL-hm1 cells is carried out analogously to the method described by KUDO and OGURA (1986) for neuronal cells. An AXIOVERT 35 fluorescence microscope made by ZEISS is used in conjunction with an imaging system made by HAMAMATSU, consisting of the ICMS-image processing system, residual light camera with control unit and image intensifier DVS 3000.

The kinetics of the cytoplasmic $Ca^{2+}$-concentration is recorded continuously as a concentration/time curve after the cell activation stimulated by Thapsigargin (0.1 μM). The curves of two activated cell cultures are compared in the presence and absence of 10 μM test substance. The area under these curves (area under the curve=AUC) is integrated and recorded as a measurement of cell activation. The inhibitory potency of the UCC-blockers tested is determined using the following equation:

$$\%H = 100 - \frac{AUC_{inh} \times 100}{AUC_{(control)}}$$

% H=the percentage inhibition of the calcium entry through unselective cation channels which is stimulated and inhibited by 10 μM of test substance.

$AUC_{inh}$=area under the curve recorded in the presence of the stimulant plus 10 μM inhibitory test substance, AUC control=area under the curve which is recorded only after the addition of the stimulant.

Literature Relating to the Above Explanations:

BARNES P. J., I. W. RODGER and N. C. THOMSON
Pathogenesis of asthma, in "ASTHMA, basic mechanisms and clinical management"
ED by P. J. BARNES; ACADEMIC PRESS, LONDON, 1988

GRYNKIEWICZ G., M. POENIE and R. Y. TSIEN
A new generation of $Ca^{2+}$-indicators with greatly improved fluorescence properties
J. BIOL. CHEM. 260: 3440–3450, 1985

HIDE, M. and M. A. BEAVEN
Calcium influx in a rat mast cell (RBL-2H3) line
J. BIOL. CHEM. 266 15221–15229, 1991

KUDO, Y. and A. OGURA
Glutamate-induced increase in intracellular $Ca^{2+}$-concentration in isolated hippocampal neurones
BR. J. PHARMACOL. 89: 191–198; 1986

PUTNEY, J. W., jr.
Capacitative Calcium entry revised
CELL CALCIUM 11: 611–624, 1990

RINK, T. J.
Receptor-mediated calcium entry
FEBS LETT. 268: 381–385, 1990

SEIFERT, R. and G. SCHULTZ
The superoxide forming NADPH oxidase of phagocytes: An enzyme system regulated by multiple mechanism
REV. PHYSIOL. BIOCHEM. PHARMACOL., Vol. 117, SPRINGER VERL., 1991

WELLS, E., C. G. JACKSON, S. T. HARPER, J. MANN and R. P. EAOY
Characterization of primate bronchoalveolar mast cells II, inhibition of histamine, $LTC_4$ and $PGF_{2a}$ release from primate bronchoalveolar mast cells and a comparison with rat peritoneal mast cells
J. IMMUNOL. 137: 3941–3945, 1986.

Results of Measurement:

The percentage inhibition of UCC after Thapsigargin stimulation (0.1 $\mu M$ Thapsigargin) in RBL-hm 1 cells is given. The uniform concentration of the-test substances is $10^{-5}$ mol).

The functional antiinflammatory effectiveness can be demonstrated by means of the following test:

Individual RBL-2H3-cells (a tumour cell line related to the mast cells) adhering to glass slides are used.

The cultivation and attachment of the RBL-2H3-cells are carried out by the method described by HIDE and BEAVEN (1991). In order to sensitise the adhesive RBL-2H3-cells the cells are incubated for 2 hours at ambient temperature with a 1:2000 diluted commercial gammaglobulin E-solution against a dinitrophenol-bovine serum albumin complex (DNP-BSA-antigen). The cells are then washed. By the addition of 0.1 ml of DNP-BSA-solution (10 $\mu g/ml$) there is a massive immunological cell activation which is mediated by a cytoplasmic $Ca^{2+}$-overload. The fluorometric calcium measurement in the cytoplasm of individual adhering RBL-2H3-cells is carried out analogously to the method described by KUDO and OGURA (1986) for neuronal cells, which is also explained hereinbefore in this specification.

The comparison used in these investigations is (10 $\mu M$) chromoglycate which brings about an approximately 50% inhibition of the antigen-induced cell activation.

In this test the above-mentioned compounds demonstrate % H values which are comparable with the values specified hereinbefore.

Tests on microcultures of various human tumour cell lines using the tetrazolium assay in order to determine the antiproliferative effect of the substances according to the invention surprisingly showed that the compound tested was 5 to 100 times more potent than the comparison substance Verapamil.

The antiproliferative effectiveness of the test substances was determined by means of the MTT test described by MOSMANN (J. IMMUNOL. METH. 65: 55–63, 1983), DENIZOT et al. (J. IMMUNOL. METH. 89: 271–277, 1986) and J. ELIASON et al. (INT. J. CANCER 46: 113–117, 1990). (MTT=[3-(4,5-dimethylthiazol-2-yl)2,5-diphenyl-tetrazolium bromide] produced by CHEMICON Inc. El Segundo, Calif., USA). This indicator is metabolised only by living cells with intact mitochondria into a blue formazane product. The following human tumour cell lines were used in our test: A 549 (adenocarcinoma of the lung), A 431 (epidermal carcinoma of the vulva), PC 3 (adenocarcinoma of the prostate), SK BR 3 (adenocarcinoma of the breast), HT 29 (CX1 1) (adenocarcinoma of the colon) and K 562 (chronic myeloid leukaemia cell).

The test was carried out on microtitre plates. Each well contained 100 $\mu l$ of a cell suspension ($0.2 \times 10^6$ cells per ml). The incubation medium used was RPMI 1640 with 10% heat-inactivated foetal calves' serum and 50 $\mu g/ml$ of gentamycin. The cell suspensions were incubated for 0, 24, 48 or 72 hours in air with a humidity at saturation point in a $CO_2$ (5%)/air (95%) mixture at 37° C., incubated in the presence and absence of variable concentrations of antiproliferative test substances. The test substances were dissolved in DMSO (final dilution: 0.1%). Then 10 $\mu l$ of MTT-solution (3 mg/ml) were added, followed after 3 hours by 100 $\mu l$ of an isopropanol solution containing 0.08 N HCl. After a further hour, the light absorption at 570 nm (comparative wavelength 630 nm) was determined in a microplate reader. The light absorption is directly proportional to the number of living cells. The half-maximum inhibitory concentrations of the substances tested were 1 $\mu g/ml$.

The vasospasmolytic effectiveness of the above-mentioned functional endothelin and Thapsigargin antagonists were confirmed on an isolated blood vessel preparation: coronary perfusion was continuously quantified, on retrogressively perfused, spontaneously beating LANDENDORFF hearts taken from rats, by means of electromagnetic flow measurement (apparatus supplied by Hugo Sachs Elektronik, MARCH). This measuring apparatus could be used to record the extent, duration and pattern of vascular spasms with a high degree of accuracy. If perfusion is carried out with 100 nM endothelin concentration, the coronary perfusion flow is reduced from 11 to 5 ml/min. The restriction in perfusion can be reversed by means of the substances according to the invention. The potencies of the compounds according to the invention with regard to Thapsigargin inhibition on fura-2-charged RBL-hm1-cells or the effectiveness of endothelin-inhibition on fura-2-charged HL 60 cells correlates clearly with the vasospasmolytic effectiveness of the test substances detected on the Langendorff preparation. It can be concluded from this that, underlying the vasospasmolytic endothelin antagonism of the substances tested, there is a blockade of the unselective cation channels.

Examples of Pharmaceutical Preparations a) Coated Tablets 1 tablet core contains:

| | |
|---|---|
| Active substance of general formula I | 30.0 mg |
| Lactose | 100.0 mg |
| Corn starch | 75.0 mg |
| Gelatine | 3.0 mg |
| Magnesium stearate | 2.0 mg |
| | 210.0 mg |

Preparation

The active substance mixed with lactose and corn starch is granulated with a 10% aqueous gelatine solution through a 1 mm mesh screen, dried at 40° C. and rubbed through a screen once more. The granules thus obtained are mixed with magnesium stearate and compressed. The cores produced in this way are coated in the usual manner with a coating consisting of an aqueous suspension of sugar, titanium dioxide, talc and gum arabic. The finished coated tablets are polished with beeswax.

b) Tablets

| | |
|---|---|
| Active substance of general formula I | 30.0 mg |
| Lactose | 100.0 mg |
| Corn starch | 70.0 mg |
| Soluble starch | 7.0 mg |
| Magnesium stearate | 3.0 mg |
| | 210.0 mg |

Preparation

The active substance and magnesium stearate are granulated with an aqueous solution of the soluble starch, the granules are dried and intimately mixed with lactose and corn starch. The mixture is then compressed into tablets weighing 210 mg.

c) Capsules

| | |
|---|---|
| Active substance according to formula I | 20.0 mg |
| Lactose | 230.0 mg |
| Corn starch | 40.0 mg |
| Talc | 10.0 mg |
| | 300.0 mg |

Preparation

The active substance, lactose and corn starch are first combined in a mixer and then in a grinding machine. The mixture is returned to the mixer, thoroughly combined with the talc and mechanically packed into hard gelatine capsules.

d) Tablets

| | |
|---|---|
| Active substance according to the invention | 40.0 mg |
| Lactose | 100.0 mg |
| Corn starch | 50.0 mg |
| Colloidal silica | 2.0 mg |
| Magnesium stearate | 3.0 mg |
| total | 195.0 mg |

Preparation

The active substance is mixed with some of the excipients and granulated with a solution of the soluble starch in water. After the granules have dried the remaining excipients are added and the mixture is compressed to form tablets.

e) Coated Tablets

| | |
|---|---|
| Active substance according to the invention | 20.0 mg |
| Lactose | 100.0 mg |
| Corn starch | 65.0 mg |
| Colloidal silica | 2.0 mg |
| Soluble starch | 5.0 mg |
| Magnesium stearate | 3.0 mg |
| total | 195.0 mg |

Preparation

The active substance and excipients are compressed to form tablet cores as described in Example a) and these are then coated in the usual way with sugar, talc and gum arabic.

f) Suppositories

| | |
|---|---|
| Active substance according to the invention | 50.0 mg |
| Lactose | 250.0 mg |
| Suppository mass q.s. ad | 1.7 g |

Preparation

The active substance and lactose are mixed together and the mixture is uniformly suspended in the molten suppository mass. The suspensions are poured into chilled moulds to form suppositories weighing 1.7 g.

g) Ampoules

| | |
|---|---|
| Active substance according to the invention | 20.0 mg |
| sodium chloride | 5.0 mg |
| Twice distilled water q.s. ad | 2.0 ml |

Preparation

The active substance and the sodium chloride are dissolved in twice distilled water and the solution is transferred under sterile conditions into ampoules.

h) Ampoules

| | |
|---|---|
| Active substance according to the invention | 10.0 mg |
| Sodium chloride | 7.0 mg |
| Twice distilled water q.s. ad | 1.0 ml | i) Drops

| | |
|---|---|
| Active substance according to the invention | 0.70 g |
| Methyl p-hydroxybenzoate | 0.07 g |
| Propyl p-hydroxybenzoate | 0.03 g |
| Demineralised water q.s. ad | 100.00 ml |

Preparation

The active substance and preservatives are dissolved in demineralised water, the solution is filtered and transferred into 100 ml vials.

What is claimed is:

1. A compound of formula I

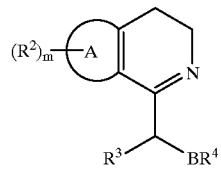

wherein

A is a indolo or thieno group and m is zero;

B is the group —O—, —S— or —CHR$^5$—, wherein R$^5$ is hydrogen, (C$_{1-6}$)alkyl, phenyl or benzyl;

R$^3$ is 2- or 3-thienyl, (C$_{4-7}$)cycloalkyl, (C$_{4-6}$)-cycloalkyl (C$_{1-5}$)alkyl or

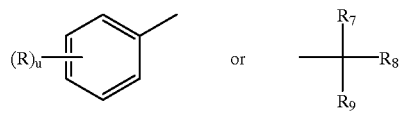

wherein:

R is (C$_{1-4}$)alkyl, hydroxy, —N$_3$, fluorine, chlorine, bromine, iodine, CF$_3$ or (C$_{1-4}$)alkoxy, u is 0, 1, 2 or 3, and R$^7$, R$^8$, and R$^9$ independently of one another are methyl, ethyl, propyl, phenyl or benzyl, but not more than two of the substituents can simultaneously be phenyl or benzyl;

R$^4$ is (a) branched or unbranched C$_{3-6}$-alkenyl which may be substituted by phenyl, or (b) branched or unbranched C$_{3-6}$-alkynyl which may be substituted by phenyl, or (c) branched or unbranched C$_{1-3}$-alkyl, wherein the alkyl may be substituted by:

(1) hydroxy,
(2) (C$_{1-4}$)alkoxy,
(3) di(C$_{1-4}$)alkylamino,
(4) furyl,
(5) pyridyl,
(6) pyrrolidinyl,
(7) N-methylpyrrolidinyl,
(8) morpholino,
(9) indolyl,
(10) nitrilo,
(11) thienyl,
(12) adamantyl,
(13) cyclohexyl,
(14) phenyl, phenoxy, or benzyloxy, wherein this phenyl group or the phenyl moiety of this group is optionally substituted by the bridge —O—CH$_2$O— or optionally mono-, di- or trisubstituted by;

(a) hydroxy,
(b) (C$_{1-4}$)alkoxy,
(c) benzyloxy,
(d) fluorine,
(e) chlorine,
(f) bromine,
(g) iodine,
(h) CF$_3$,
(i) N$_3$,
(j) NO$_2$,
(k) (C$_{1-4}$)alkyl,
(l) adamantyl,
(m) —SO$_2$NH$_2$,
(n) NHCOCH$_3$,
(o) —NHSO$_2$CH$_3$, or
(p) —C(O)O—R$_{14}$, wherein R$_{14}$ is (C$_{3-7}$) cycloalkyl or branched or unbranched (C$_{1-6}$) alkyl, whilst the alkyl is optionally substituted by phenyl, and this phenyl may be mono- to trisubstituted by fluorine, chlorine, bromine, iodine, CF$_3$, C$_1$- or C$_2$-alkyl, or C$_1$- or C$_2$-alkoxy,

(15) naphthyloxy, or
(16) 2 unsubstituted phenyl groups; or, (d)

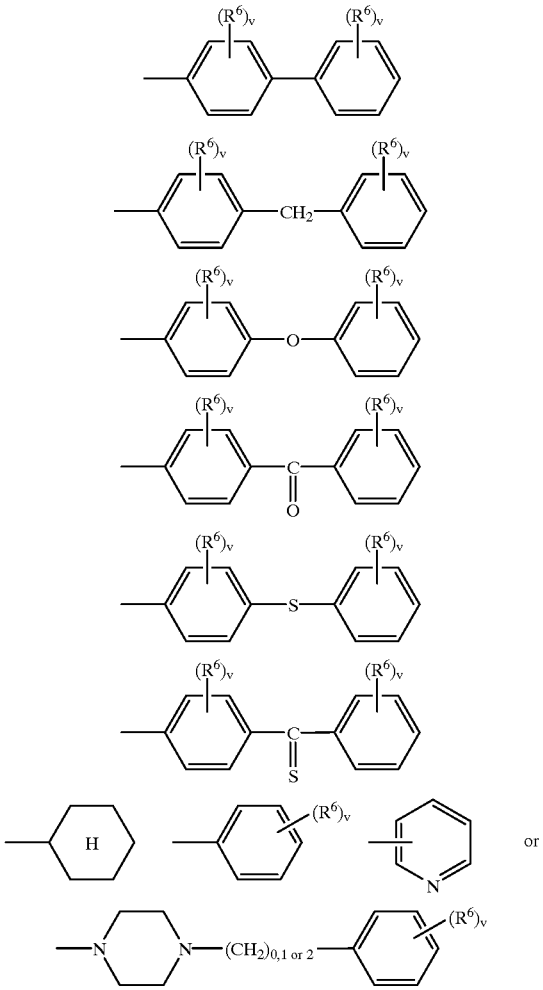

wherein R$^6$ is (C$_{1-4}$)alkyl, hydroxy, —N$_3$, fluorine, chlorine, bromine, iodine, CF$_3$, NO$_2$ or (C$_{1-4}$)alkoxy and v is 0, 1, 2 or 3, or the salts thereof with physiologically acceptable acids or complexing agents.

2. The compound as recited in claim 1, wherein R$^4$ has one of the following meanings:

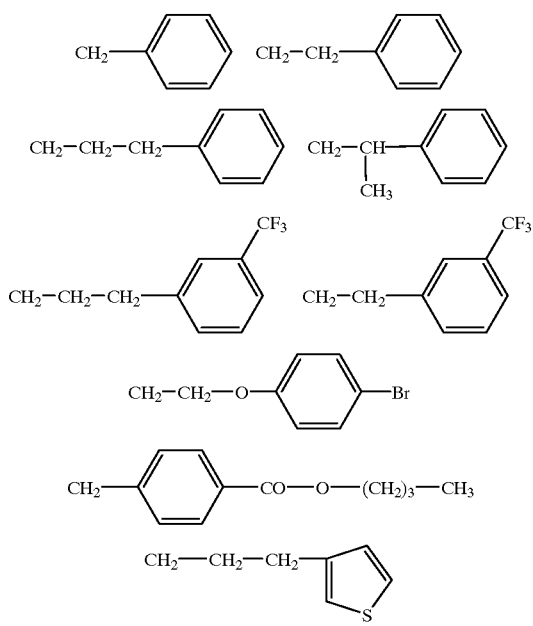
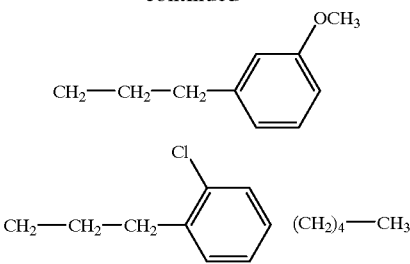
3. The compound as recited in claim 1, wherein $R^3$ is phenyl or cyclohexyl.
4. The compound as recited in claim 1, wherein B is O or $CH_2$.
5. A pharmaceutical preparation comprising a compound as recited in claim 1 together with a pharmaceutically acceptable carrier.
* * * * *